United States Patent
McKenna

(10) Patent No.: US 11,033,710 B1
(45) Date of Patent: Jun. 15, 2021

(54) THERAPY SYSTEM AND METHODS

(71) Applicant: Avalon BIMM, LLC, San Diego, CA (US)

(72) Inventor: William McKenna, San Diego, CA (US)

(73) Assignee: Avalon BIMM, LLC., San Diego, CA (US)

( * ) Notice: Subject to any disclaimer, the term of this patent is extended or adjusted under 35 U.S.C. 154(b) by 160 days.

(21) Appl. No.: 16/243,512

(22) Filed: Jan. 9, 2019

Related U.S. Application Data

(60) Provisional application No. 62/615,401, filed on Jan. 9, 2018.

(51) Int. Cl.
  *A61M 21/02* (2006.01)
  *A63B 37/12* (2006.01)
  *A63B 41/08* (2006.01)
  *A61M 21/00* (2006.01)

(52) U.S. Cl.
  CPC ............. *A61M 21/02* (2013.01); *A63B 37/12* (2013.01); *A63B 41/08* (2013.01); *A61M 2021/0044* (2013.01); *A61M 2205/056* (2013.01); *A61M 2205/59* (2013.01); *A63B 2209/00* (2013.01); *A63B 2213/00* (2013.01)

(58) Field of Classification Search
  CPC .......... A61M 21/02; A61M 2021/0044; A61M 2205/056; A61M 2205/59; A63B 37/12; A63B 41/08; A63B 2209/00; A63B 2213/00
  USPC ................................ 600/26–28; 128/897–899
  See application file for complete search history.

(56) References Cited

U.S. PATENT DOCUMENTS

| | | | | |
|---|---|---|---|---|
| 6,224,513 | B1* | 5/2001 | Chow | A63B 23/16 473/601 |
| 7,815,878 | B1* | 10/2010 | Wheatley | A63B 43/00 422/306 |
| 2002/0103429 | A1* | 8/2002 | deCharms | A61B 5/4094 600/410 |

(Continued)

OTHER PUBLICATIONS

Chokron S, Dutton GN. Impact of Cerebral Visual Impairments on Motor Skills: Implications for Developmental Coordination Disorders. Front Psychol. Oct. 4, 2016;7:1471. doi: 10.3389/fpsyg.2016. 01471. PMID: 27757087; PMCID: PMC5048540. (Year: 2016).*

(Continued)

*Primary Examiner* — Navin Natnithithadha
*Assistant Examiner* — Sunita Reddy

(57) ABSTRACT

System and methods for therapy involving the use of three-dimensional articles of manufacture having printed media at predetermined locations thereon to overcome a therapeutic issue, such as (but not necessarily limited to) fear, phobias, trauma, addiction, grief, depression, feelings of loss, physical pain and diabetic neuropathy. By using the system and methods of the present invention while focusing on emotional and/or physical pain associated with a therapeutic issue, both hemispheres of the brain are activated and random stimulation via place or grid cells and their associated complex circuits occur, which collectively causes or creates new neural connections in the brain of the patient to thereby diminish or even resolve the emotional and/or physical pain associated with the therapeutic issue.

18 Claims, 6 Drawing Sheets

(56) References Cited

U.S. PATENT DOCUMENTS

| | | | | |
|---|---|---|---|---|
| 2012/0071281 | A1* | 3/2012 | Heland | A63H 33/18 |
| | | | | 473/569 |
| 2013/0211277 | A1* | 8/2013 | Berg | A61B 5/053 |
| | | | | 600/547 |
| 2017/0106249 | A1* | 4/2017 | Marton | A63B 21/0004 |

OTHER PUBLICATIONS

Machado S., Cunha M., Portella C. E., Silva J. G., Velasques B., Bastos V. H., et al. (2008). Integration of cortical areas during performance of a catching ball task. Neurosci. Lett. 446 7-10. 10.1016/j.neulet.2008.09.036 (Year: 2008).*

Demirakca T, Cardinale V, Dehn S, Ruf M, Ende G. The Exercising Brain: Changes in Functional Connectivity Induced by an Integrated Multimodal Cognitive and Whole-Body Coordination Training. Neural Plast. 2016;2016:8240894. doi: 10.1155/2016/8240894. Epub Dec. 27, 2015. PMID: 26819776; PMCID: PMC4706972. (Year: 2016).*

* cited by examiner

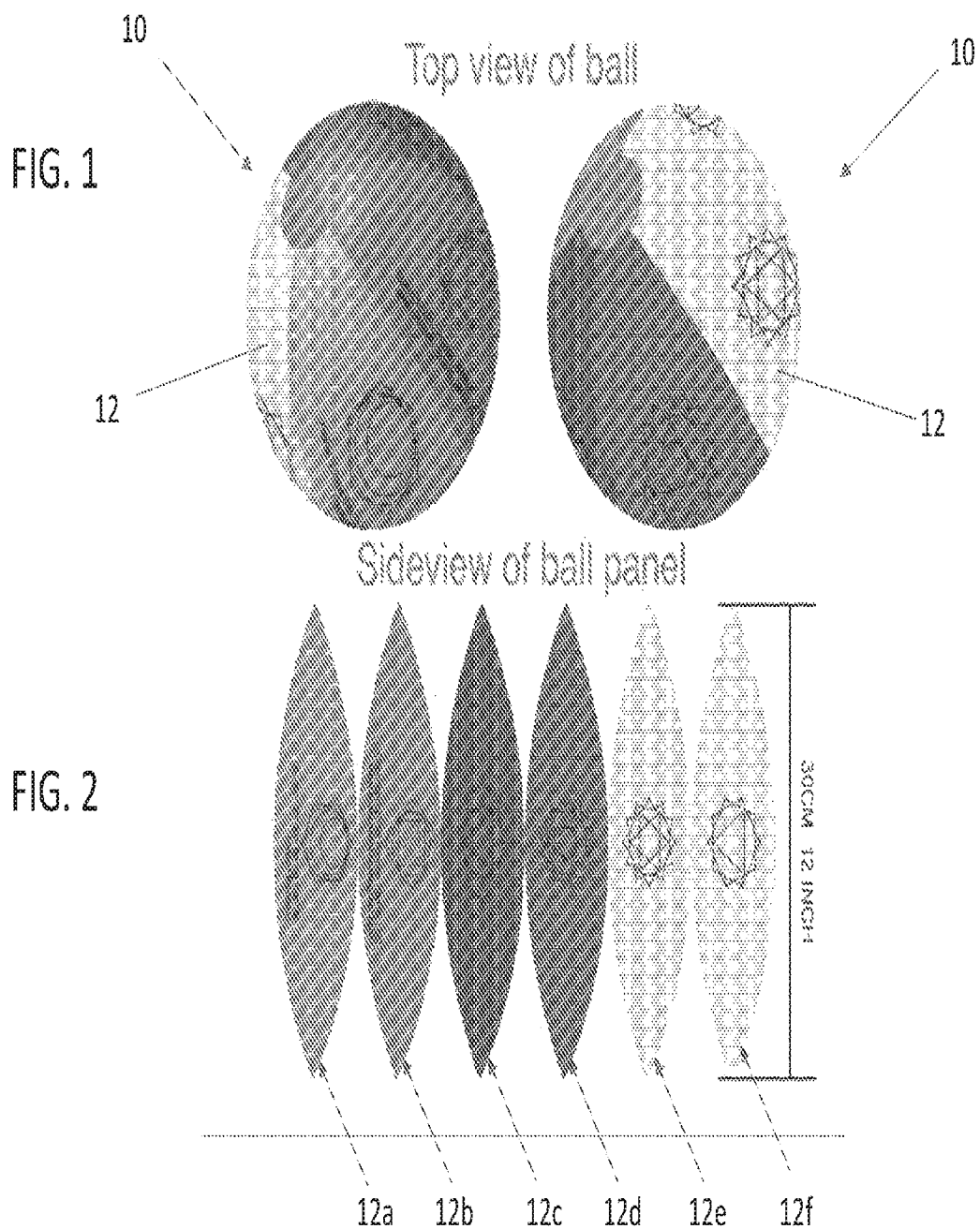

THERAPY SYSTEM AND METHODS

BACKGROUND OF THE INVENTION

I. Field of the Invention

The present invention relates generally to therapy and, more particularly, to a system and methods for therapy involving the use of three-dimensional articles of manufacture having printed media at predetermined locations thereon to overcome fear, phobias, trauma, addiction, grief, depression, feelings of loss, physical pain and neuropathy.

II. Discussion of the Prior Art

Currently billions of dollars are spent annually to treat medical and emotional effects of stress. Billions more are spent on pain management, PTSD, weight management, addictions, emotional pain of a broken heart, grief and depression. The economic loss of unemployment related to these is compounded by its effects on family and friends who care for the affected. The side effect of many of the drugs used to treat the myriad illnesses related to the above can have serious undesired consequences including death and suicide. A solution that is effective, long lasting, not drug based, does not require a medical professional's time, and can be self-administered does not currently exist. The present invention is directed at this unmet need.

SUMMARY OF THE INVENTION

The present invention accomplishes this goal by providing three-dimensional (3D) articles of manufacture having printed media at predetermined locations thereon for use in therapy to overcome fear, phobias, trauma, addition, grief, depression, feelings of loss, physical pain, and/or neuropathy. In one embodiment, the 3D article of manufacture may comprise a ball of any suitable construction (e.g. inflatable, solid, etc.) and shape (e.g. sphere-shaped, oblong, smooth curved surfaces, flat paneled surfaces, etc.). The printed media on the ball may comprise any number of alpha-numeric indicia and/or graphics, including but not limited to colors and symbols commonly referred to as chakras. The predetermined locations on the ball may comprise color panels with a predetermined chakra disposed thereon. The ball may have any number of suitable color schemes, including (but not limited to) a white ball with colored panels and/or colored chakras, a colored ball with white panels with colored chakras, etc.

The therapeutic goal of the ball (the use of which will be described below) includes but isn't necessarily limited to overcoming fear, phobias, trauma, addiction, cravings, obsessive-compulsive disorder, grief, depression, feelings of loss, physical pain, and/or diabetic neuropathy. To accomplish these goals, the ball may be used by the patient as follows:

1. Patient is in standing position with head and face pointed straight forward.
2. While maintaining head and face in the straight forward position of step (1), the patient looks down with eyes-only and focuses on a therapeutic issue (e.g. fear, phobia, trauma, addiction, grief, depression, feeling of loss, physical pain, diabetic neuropathy, etc.).
3. Patient characterizes the intensity of the emotional, physical pain or desire associated with the therapeutic issue focused on in step (2) on a scale of 1 to 10 with 1 as the lowest intensity and 10 as the highest intensity.
4. Patient brings eyes back to neutral position, looking straight forward at the ball located generally in front of the patient (approximately 90% of focus will be on the therapeutic issue and 10% will be on the ball).
5. The ball is tossed back and forth across the mid-sagittal plane of the patient (plane that separates the left side from right side of the body) and each time the patient catches the ball with both hands. The ball may be tossed by the patient and/or a third party (e.g. caregiver, therapist, etc.), whether directly to the patient (e.g. patient tosses to himself/herself and/or third party throws to the patient) or indirectly to the patient (e.g. patient or third party bounces the ball off a wall and/or floor to the patient).
6. For each catch, the patient will identify the color they see on the ball and say it aloud.
7. Repeat steps 5-6 for a therapeutically effective time period, for example between 1 and 30 minutes, with 10 to 15 minutes as one exemplary range.
8. Optional step: While standing, patient takes notice of the centerline of his/her body both front and back for optional analysis to understand the core issue after the therapy.
9. Patient characterizes intensity of the emotional, physical pain or desire of the therapeutic issue on a scale of 1 to 10.
10. If intensity characterization of step 9 is a zero (0), the process is complete. If not, the patient repeats steps 5, 6, 7, optionally 8, and 9 until intensity characterization is sufficiently reduced or approximately zero (0).

The system and methods of the present invention are effective at minimizing and/or alleviating the target issue based on the following. The left hemisphere of the brain identifies colors and symbols, while the right hemisphere of the brain identifies three-dimensional objects and where they are at in space and time. The system and methods of the present invention activate both hemispheres of the brain when the patient's eyes follow the therapy ball during the trans-sagittal movement of the ball (step 5) followed by the identification of the color after each two-handed grasp of the ball (step 6). Beyond this dual-hemisphere activation, so-called "place cells" or "grid cells" within the brain of the patient are stimulated each time the therapy ball is caught in order to remember or capture the location in space where the ball was physically caught (x, y, and z coordinates relative to the patient). Place or grid cells do not operate alone but are part of a complex circuit that gives humans our visuospatial representation. By using the system and methods of the present invention while focusing on a target issue (such as an emotional or physical pain), the stimulation of both hemispheres of the brain along with random stimulation via place or grid cells and their associated complex circuits cause new neural connections in the brain of the patient enabling the issue to be diminished or even resolved.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 1 shows a therapeutic ball of the present invention as viewed generally from a top perspective according to various aspects of the present invention;

FIG. 2 shows a side view of the various panels forming the therapeutic ball of FIG. 1 according to various aspects of the present invention;

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The therapy ball and methods disclosed herein boasts a variety of inventive features and components that warrant patent protection, both individually and in combination.

The present invention is a therapy system and related methods for overcoming fear, phobias, trauma, addiction, cravings, grief, obsessive-compulsive disorder, depression, feelings of loss, physical pain, and/or diabetic neuropathy, which includes a three-dimensional (3D) article of manufacture having printed media at predetermined locations thereon utilized by a patient according to various steps in order to lessen or alleviate the given therapeutic issue (e.g. fear, pain, etc.). The 3D article of manufacture may comprise any number of suitable structures, including but not limited to a ball of any suitable construction (e.g. inflatable, solid, etc.) and shape (e.g. sphere-shaped, oblong, smooth curved surfaces, flat paneled surfaces, etc.).

Figure 3:
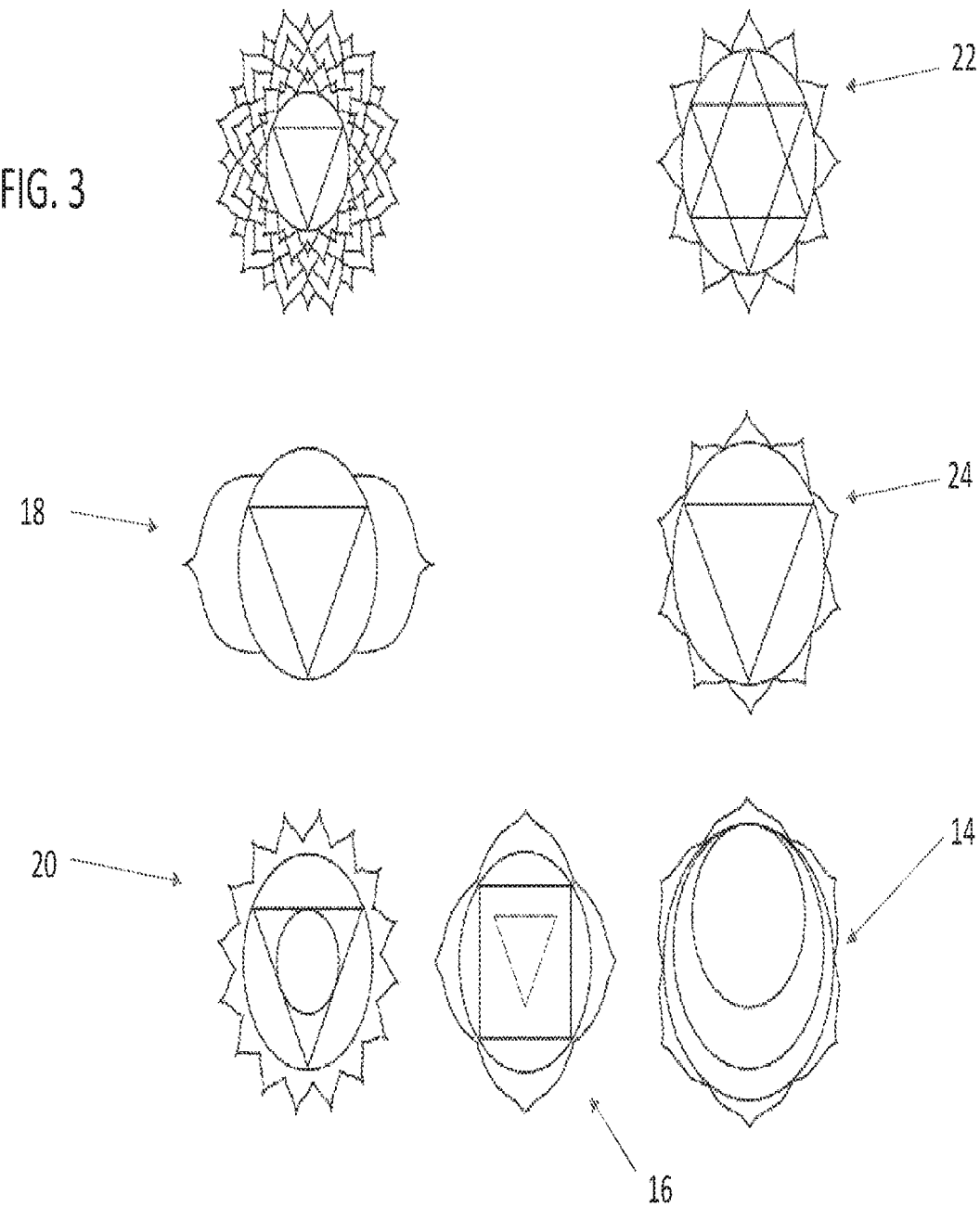
FIG. 3 shows top views of exemplary chakras suitable for placement at predetermined locations on a therapy ball according to various aspects of the present invention.
Figure 4:
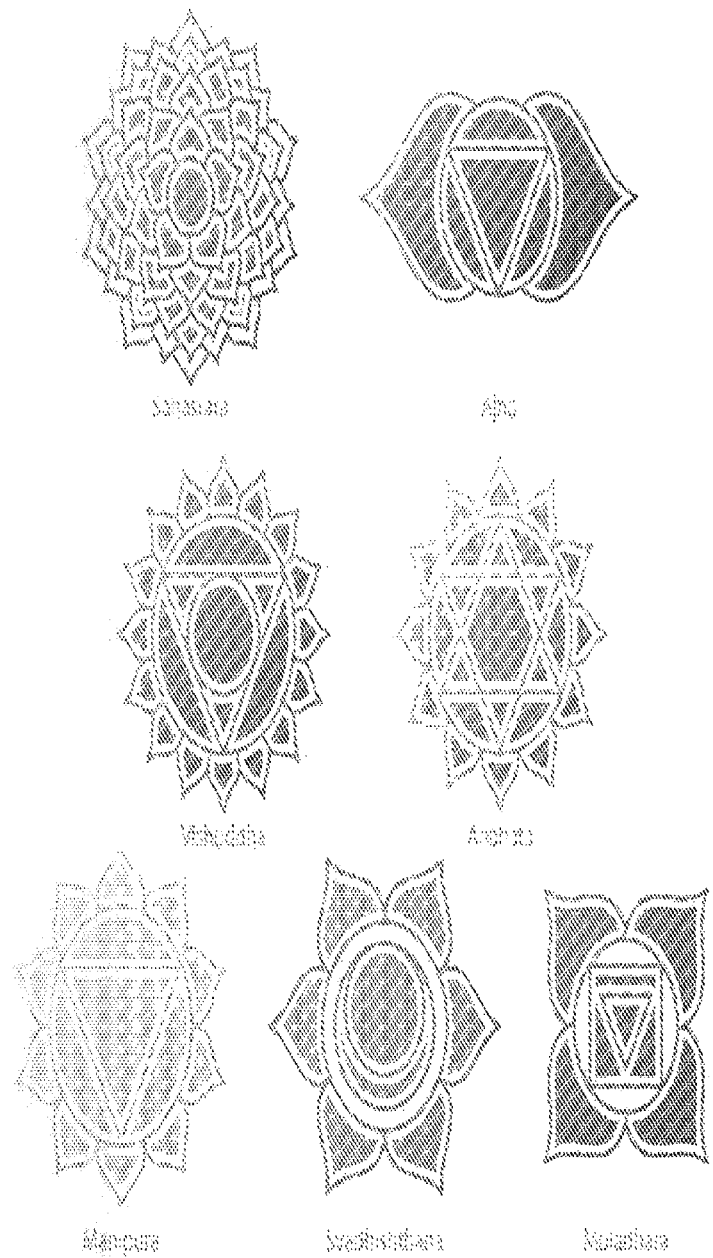
FIG. 4 shows top views of additional exemplary chakras suitable for placement at predetermined locations on a therapy ball according to various aspects of the present invention.
Figure 5:
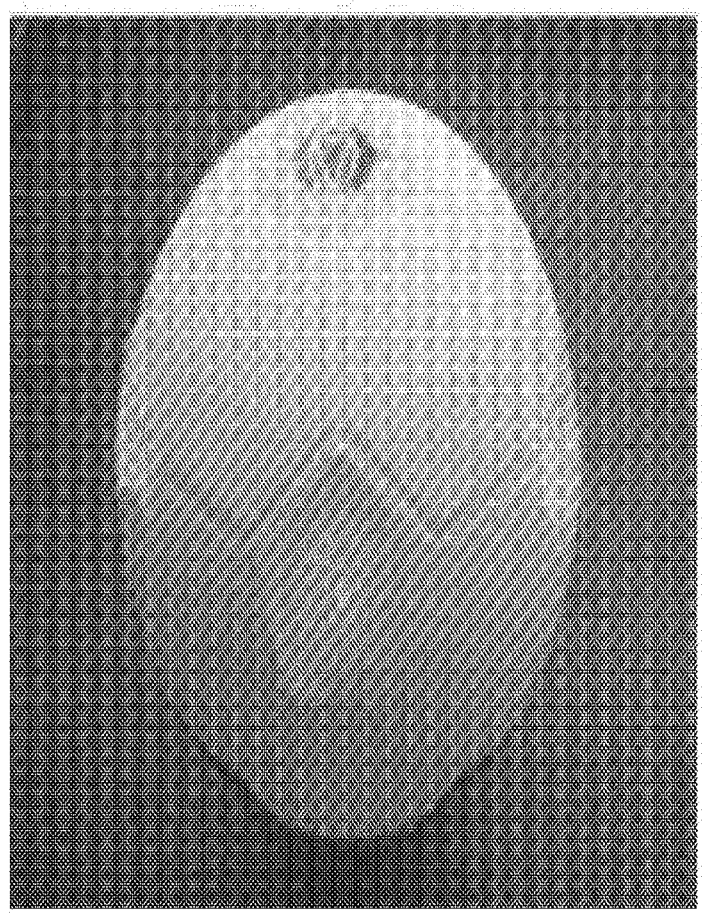
FIG. 5 shows a therapy ball according to another embodiment of the present invention, with colored chakras on a white ball according to various aspects of the present invention.

FIG. 1 illustrates a therapy ball 10 according to one representative embodiment of the present invention. The therapy ball 10 includes a plurality of panels 12 (by way of example, six) each having alpha-numeric indicia and/or graphics disposed thereon, such as (by way of example only) chakras 14, 16, 18, 20, 22, 24 located on panels 12a, 12b, 12c, 12d, 12e, 12f, respectively. Chakras 14-24 are illustrated in greater detail in FIGS. 3-4, both as disposed on the surface of the respective panels 12a-12f (FIG. 2) and separately (FIGS. 3-4). Any number of suitable colors may be used for the panels 12a-12f, including but not limited to orange for panel 12a, red for panel 12b, purple for panel 12c, blue for panel 12d, light green for panel 12e, and yellow for panel 12f. Any number of suitable chakras may be used, including but not limited to those shown in FIGS. 1-2 as well as the alternate versions shown in FIGS. 3-4. While shown as a sphere, it will be appreciated that the therapy ball 10 may have any number of additional geometric shapes without departing from the scope of the present invention, including but not limited to a truncated icosahedron, polyhedron, partially spherical and partially polyhedronal, etc.

The therapy ball 10 may employ any number of color-schemes, including (but not limited to) colored panels 12 with the chakras 14-22 in black (as shown in FIGS. 1-2) or with a white background and colored chakras (not shown). The therapy ball 10 can be made out of any material appropriate to playing catch with, including (but not limited to) a beach-ball construction, common playground/kickball construction, plush/soft construction, soccer type ball, fabric exterior, cotton fill, etc. While shown with six (6) panels 12a-12f, it will be understood that any number of panels and chakras may be provided without departing from the scope of the present invention.

The therapy ball 10 may be used to accomplish a therapeutic goal such as (but not limited to) overcoming fear, phobias, trauma, addiction, cravings, obsessive-compulsive disorder, grief, depression, feelings of loss, physical pain, and/or diabetic neuropathy. For any of these, the patient is to perform the following steps:

1. Patient is in standing position with head and face pointed straight forward.
2. While maintaining head and face in the straight forward position of step (1), the patient looks down with eyes-only and focuses on a therapeutic issue (e.g. fear, phobia, trauma, addiction, grief, depression, feeling of loss, physical pain, diabetic neuropathy, etc.).
3. Patient characterizes the intensity of the emotional, physical pain or desire associated with the therapeutic issue focused on in step (2) on a scale of 1 to 10 with 1 as the lowest intensity and 10 as the highest intensity.
4. Patient brings eyes back to neutral position, looking straight forward at the ball located generally in front of the patient (approximately 90% of focus will be on the therapeutic issue and 10% will be on the ball).
5. The ball is tossed back and forth across the mid-sagittal plane of the patient (plane that separates the left side from right side of the body) and each time the patient catches the ball with both hands. This is referred to as "trans-sagittal" ball movement. Trans-sagittal ball movement may be accomplished by the patient and/or a third party (e.g. caregiver, therapist, etc. . . . ), whether directly to the patient (e.g. patient tosses to himself/herself and/or third party throws to the patient) or indirectly to the patient (e.g. patient or third party bounces the ball off a wall and/or floor to the patient).
6. For each catch, the patient will identify the color they see on the ball and say it aloud.
7. Repeat steps 5-6 for a therapeutically effective time period, for example between 1 and 30 minutes, with 10 to 15 minutes as one exemplary range.
8. Optional step: While standing, patient takes notice of the centerline of his/her body both front and back for optional analysis to understand the core issue after the therapy.
9. Patient characterizes intensity of the emotional, physical pain or desire of the therapeutic issue on a scale of 1 to 10.
10. If intensity characterization of step 9 is a zero (0), the process is complete. If not, the patient repeats steps 5, 6, 7, optionally 8, and 9 until intensity characterization is sufficiently reduced or approximately zero (0).

The patient may perform the therapeutic method by themselves and/or with a partner without the need of professional medical guidance or intervention. The patient will typically experience the sensation of heat, pain and release somewhere along the sagittal plane (centerline) of the physical body and relief from the emotion as well. For example, a patient will have a changed energy level before therapy and after therapy.

The effectiveness of the therapy ball 10 used according to the above-described method is based on a combination of: a) the color of the therapy ball 10, b) the various chakras 14-24, and c) the random nature of the trans-sagittal movement and catching process of the therapy ball 10. The left hemisphere of the brain identifies colors and symbols, while the right hemisphere of the brain identifies three-dimensional objects and where they are at in space and time. The system and methods of the present invention activate both hemispheres of the brain when the patient's eyes follow the therapy ball during the trans-sagittal movement of the ball (step 5) followed by the identification of the color after each two-handed grasp of the ball (step 6). Beyond this dual-hemisphere activation, so-called "place cells" or "grid cells" within the brain of the patient are stimulated each time the therapy ball is caught in order to remember or capture the location in space where the ball was physically caught (x, y, and z coordinates relative to the patient). Place or grid cells do not operate alone but are part of a complex circuit that gives humans our visuospatial representation. By using the system and methods of the present invention while focusing on a target issue (such as an emotional or physical pain), the stimulation of both hemispheres of the brain along with random stimulation via place or grid cells and their associated complex circuits cause new neural connections in the brain of the patient enabling the issue to be diminished or even resolved.

Figure 6:
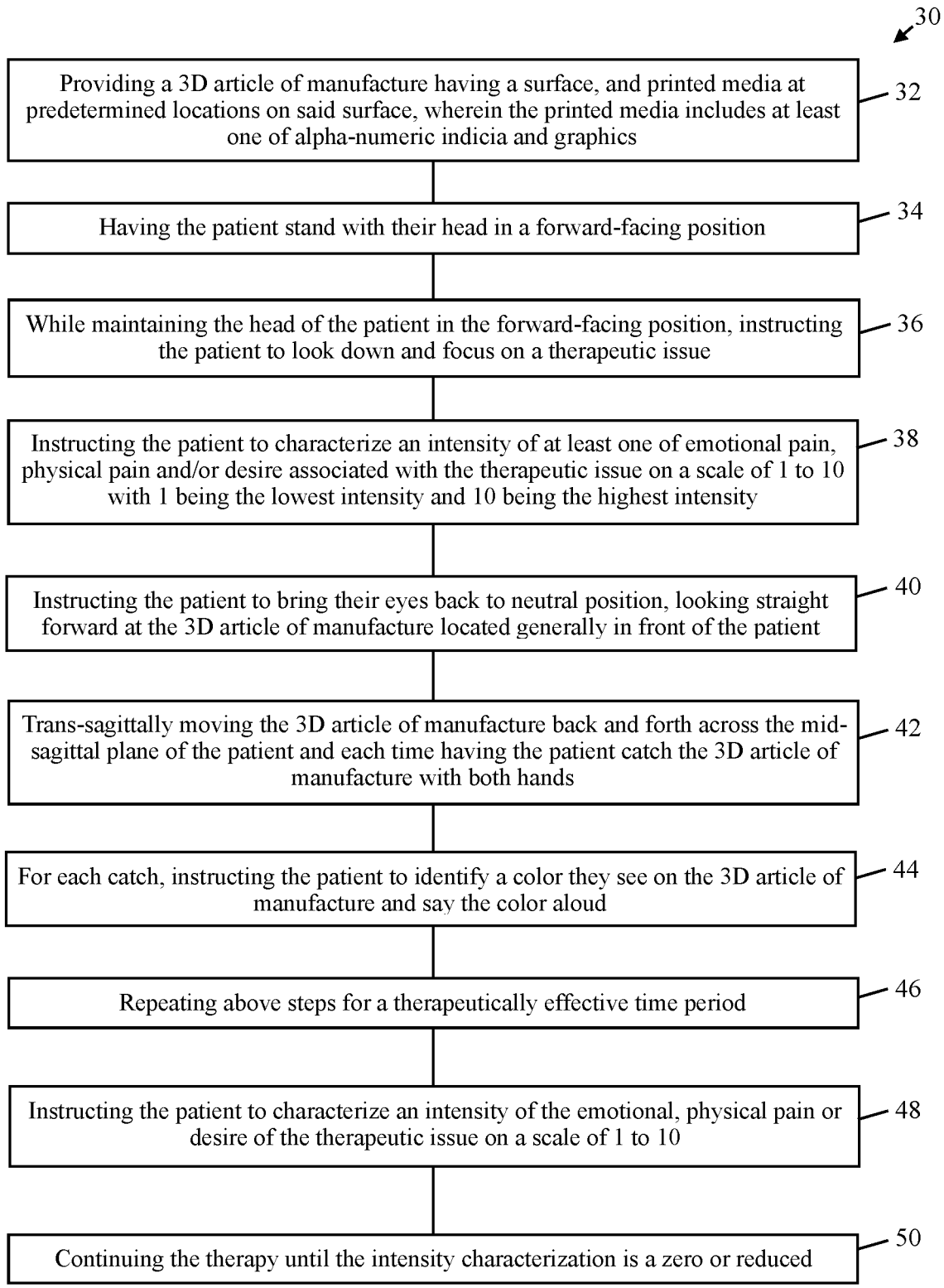
FIG. 6 is a flowchart illustrating a method of treating a patient experiencing a therapeutic issue according to various aspects of the present invention.

As illustrated by way of example only in FIG. 6, in some embodiments, a method 30 of treating a patient experiencing a therapeutic issue comprising several steps to define a therapy is disclosed. In some embodiments, a first step 32 of the method 30 comprises providing a three-dimensional (3D) article of manufacture having a surface, printed media at predetermined locations on said surface, wherein said printed media includes at least one of alpha-numeric indicia and graphics. In some embodiments, another step 34 of the method 30 comprises having the patient stand with their head in a forward-facing position. In some embodiments, another step 36 of the method 30 comprises: while maintaining the head of the patient in the forward-facing position of step 34, instructing the patient to look down and focus on said therapeutic issue. In some embodiments, another step 38 of the method 30 comprises instructing the patient to characterize an intensity of at least one of emotional pain, physical pain and/or desire associated with the therapeutic issue focused on in step 36 on a scale of 1 to 10 with 1 being the lowest intensity and 10 being the highest intensity. In some embodiments, another step 40 of the method 30 comprises instructing the patient to bring their eyes back to neutral position, looking straight forward at the 3D article of manufacture located generally in front of the patient. In some embodiments, another step 42 of the method 30 comprises trans-sagittally moving the 3D article of manufacture back and forth across the mid-sagittal plane of the patient and each time having the patient catch the 3D article of manufacture with both hands. In some embodiments, another step 44 of the method 30 comprises: for each catch, instructing the patient to identify a color they see on the 3D article of manufacture and say the color aloud. In some embodiments, another step 46 of the method 30 comprises repeating the previous steps for a therapeutically effective time period. In some embodiments, another step 48 of the method 30 comprises instructing the patient to characterize an intensity of the emotional, physical pain or desire of the therapeutic issue on a scale of 1 to 10. In some embodiments, another step 50 of the method 30 comprises continuing the therapy until said intensity characterization is a zero or reduced.

Figure 7:
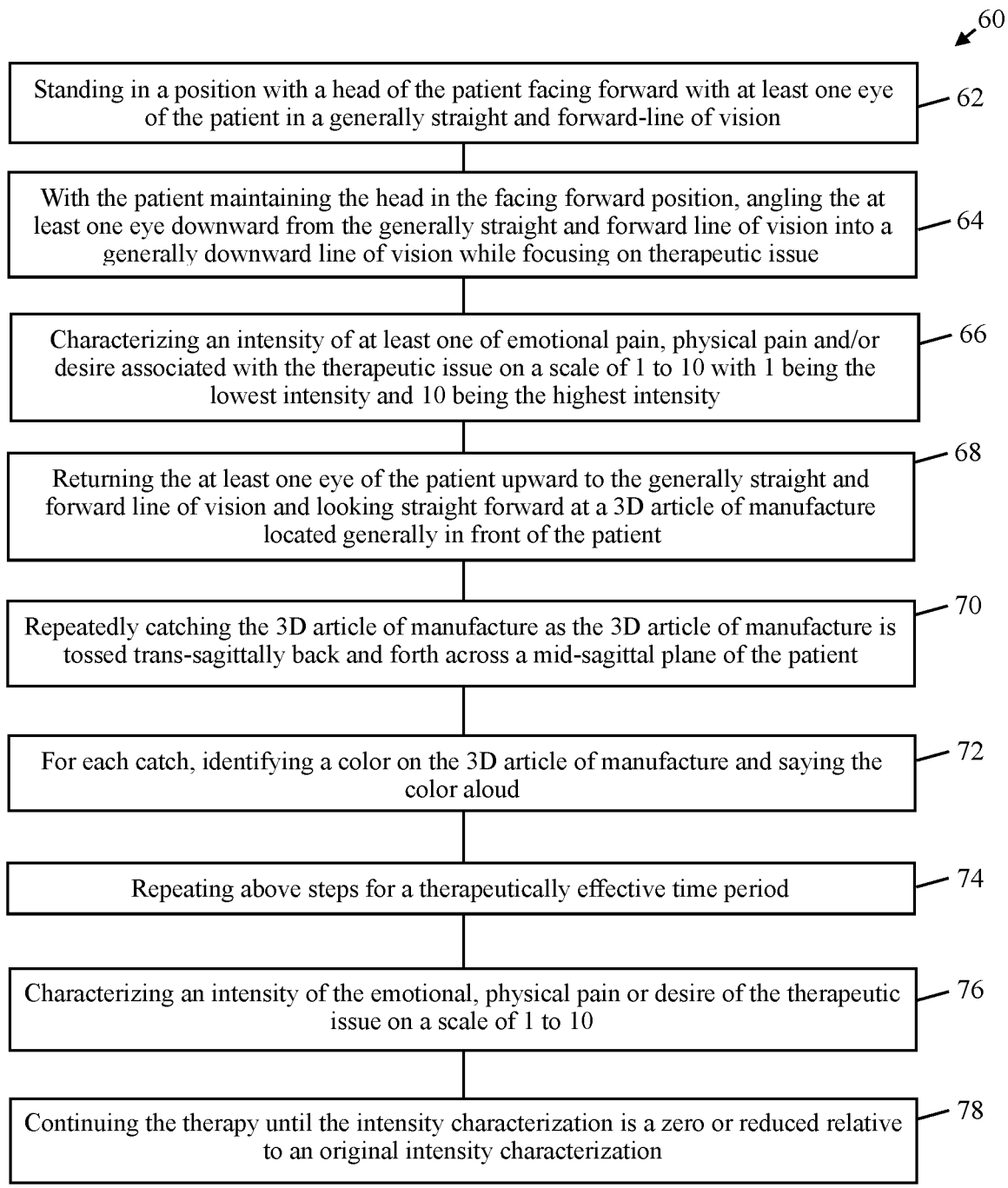
FIG. 7 is a flowchart illustrating a method of treating a patient experiencing a therapeutic issue using a three-dimensional (3D) article of manufacture having a surface and printed media comprising at least one of alphanumeric indicia and graphics at predetermined locations on said surface according to various aspects of the present invention.

As illustrated by way of example only in FIG. 7, in some embodiments, a method 60 of treating a patient experiencing a therapeutic issue issue using a three-dimensional (3D) article of manufacture having a surface and printed media comprising at least one of alphanumeric indicia and graphics at predetermined locations on said surface and comprising several steps to define a therapy is disclosed. In some embodiments, a first step 62 of the method 60 comprises standing in a position with a head of the patient facing forward with at least one eye of the patient in a generally straight and forward line of vision. In some embodiments, another step 64 of the method 60 comprises: with the patient maintaining the head in the facing forward position of the previous step 62, angling the at least one eye downward from the generally straight and forward line of vision into a generally downward line of vision while focusing on the therapeutic issue. In some embodiments, another step 66 of the method 60 comprises characterizing an intensity of at least one of emotional pain, physical pain and/or desire associated with the therapeutic issue focused on in the previous step 64 on a scale of 1 to 10 with 1 being the lowest intensity and 10 being the highest intensity. In some embodiments, another step 68 of the method 60 comprises returning the at least one eye of the patient upward to the generally straight and forward line of vision and looking straight forward at the 3D article of manufacture located generally in front of the patient. In some embodiments, another step 70 of the method 60 comprises repeatedly catching the 3D article of manufacture as the 3D article of manufacture is tossed trans-sagittally back and forth across a mid-sagittal plane of the patient. In some embodiments, another step 72 of the method 60 comprises: for each catch of the previous step 70, identifying a color on the 3D article of manufacture and saying the color aloud. In some embodiments, another step 74 of the method 60 comprises repeating the previous steps for a therapeutically effective time period. In some embodiments, another step 76 of the method 60 comprises characterizing an intensity of the emotional, physical pain or desire of the therapeutic issue on a scale of 1 to 10. In some embodiments, another step 78 of the method 60 comprises continuing the therapy until the intensity characterization is a zero or reduced relative to an original intensity characterization.

The therapy systems and methods set forth herein overcome or at least improve upon the unmet need in the prior art. From the foregoing disclosure and detailed description of certain preferred embodiments, it is also apparent that various modifications, additions and other alternative embodiments are possible without departing from the true scope and spirit of the present invention. The embodiments discussed were chosen and described to provide the best illustration of the principles of the present invention and its practical application to thereby enable one of ordinary skill in the art to utilize the invention in various embodiments and with various modifications as are suited to the particular use contemplated. All such modifications and variations are within the scope of the present invention as determined by the appended claims when interpreted in accordance with the benefit to which they are fairly, legally, and equitably entitled.

What is claimed is:

1. A method of treating a patient experiencing a therapeutic issue, comprising the following steps to define a therapy:
 (a) providing a three-dimensional (3D) article of manufacture having a surface, printed media at predetermined locations on said surface, wherein said printed media includes at least one of alpha-numeric indicia and graphics;
 (b) having the patient stand with their head in a forward-facing position;
 (c) while maintaining the head of the patient in the forward-facing position of step (b), instructing the patient to look down and focus on said therapeutic issue;
 (d) instructing the patient to characterize an intensity of at least one of emotional pain, physical pain and/or desire associated with the therapeutic issue focused on in step (c) on a scale of 1 to 10 with 1 being the lowest intensity and 10 being the highest intensity;
 (e) instructing the patient to bring their eyes back to neutral position, looking straight forward at the 3D article of manufacture located generally in front of the patient;
 (f) trans-sagittally moving said 3D article of manufacture back and forth across the mid-sagittal plane of the patient and each time having the patient catch the 3D article of manufacture with both hands;
 (g) for each catch, instructing the patient to identify a color they see on the 3D article of manufacture and say said color aloud;
 (h) repeating steps (a)-(g) for a therapeutically effective time period;
 (i) instructing the patient to characterize an intensity of the emotional, physical pain or desire of the therapeutic issue on a scale of 1 to 10; and
 (j) continuing the therapy until said intensity characterization is a zero or reduced.

2. The method of claim 1 and further, wherein said 3D article of manufacture is a ball.

3. The method of claim 2 and further, wherein said ball has a construction that is at least one of inflatable and/or solid.

4. The method of claim 3 and further, wherein said ball has a shape that is at least one of sphere-shaped and oblong, wherein said surface is at least one of a smooth curved surface and a flat paneled surface.

5. The method of claim 4 and further, wherein said graphics comprises chakras.

6. The method of claim 1 and further, wherein said therapeutic issue comprises at least one of fear, phobias, trauma, addiction, cravings, grief, obsessive-compulsive disorder, depression, feelings of loss, physical pain, and diabetic neuropathy.

7. The method of claim 1 and further, wherein trans-sagittal movement of said 3D article of manufacture is accomplished by at least one of said patient and a third party.

8. The method of claim 1 and further, wherein said trans-sagittal movement of said 3D article of manufacture to said patient is at least one of direct and indirect.

9. The method of claim 1 and further, wherein said therapeutically effective time period is between 1 minute and 30 minutes.

10. A method of treating a patient experiencing a therapeutic issue using a three-dimensional (3D) article of manufacture having a surface and printed media comprising at least one of alphanumeric indicia and graphics at predetermined locations on said surface, comprising the patient performing the following steps to define a therapy:
 a) standing in a position with a head of the patient facing forward with at least one eye of the patient in a generally straight and forward line of vision;
 b) with the patient maintaining the head in the facing forward position of step (a), angling the at least one eye downward from the generally straight and forward line of vision of step (a) into a generally downward line of vision while focusing on said therapeutic issue;
 c) characterizing an intensity of at least one of emotional pain, physical pain and/or desire associated with the therapeutic issue focused on in step (b) on a scale of 1 to 10 with 1 being the lowest intensity and 10 being the highest intensity;
 d) returning the at least one eye of the patient upward to the generally straight and forward line of vision and looking straight forward at the 3D article of manufacture located generally in front of the patient;
 e) repeatedly catching the 3D article of manufacture as the 3D article of manufacture is tossed trans-sagittally back and forth across a mid-sagittal plane of the patient;
 f) for each catch of step (e), identifying a color on the 3D article of manufacture and saying the color aloud;
 g) repeating steps (a)-(f) for a therapeutically effective time period;
 h) characterizing an intensity of the emotional, physical pain or desire of the therapeutic issue on a scale of 1 to 10; and
 i) continuing the therapy until said intensity characterization is a zero or reduced relative to an original intensity characterization.

11. The method of claim 10 and further, wherein said 3D article of manufacture is a ball.

12. The method of claim 11 and further, wherein said ball has a construction that is at least one of inflatable and/or solid.

13. The method of claim 12 and further, wherein said ball has a shape that is at least one of sphere-shaped and oblong, wherein said surface is at least one of a smooth curved surface and a flat paneled surface.

14. The method of claim 13 and further, wherein said graphics comprises chakras.

15. The method of claim 10 and further, wherein said therapeutic issue comprises at least one of fear, phobias, trauma, addiction, cravings, grief, obsessive-compulsive disorder, depression, feelings of loss, physical pain, and diabetic neuropathy.

16. The method of claim 10 and further, wherein trans-sagittal movement of said 3D article of manufacture is accomplished by at least one of said patient and a third party.

17. The method of claim 10 and further, wherein said trans-sagittal movement of said 3D article of manufacture to said patient is at least one of direct and indirect.

18. The method of claim 10 and further, wherein said therapeutically effective time period is between 1 minute and 30 minutes.

* * * * *